(12) United States Patent
Orth et al.

(10) Patent No.: US 6,827,933 B2
(45) Date of Patent: Dec. 7, 2004

(54) IMMUNOGENIC COMPOSITIONS OF HUMAN PAPILLOMAVIRUS AND SERA PRODUCED THEREFROM

(75) Inventors: Gerard Orth, Sceaux (FR); Sylvie Beaudenon, Esbly (FR); Michel Favre, Paris (FR); Dina Kremsdorf, Paris (FR); Odile Croissant, Paris (FR); Gerard Pehau-Arnaudet, Montreuil (FR)

(73) Assignee: Roche Molecular Systems, Inc., Alameda, CA (US)

( * ) Notice: Subject to any disclaimer, the term of this patent is extended or adjusted under 35 U.S.C. 154(b) by 0 days.

(21) Appl. No.: 09/987,557

(22) Filed: Nov. 15, 2001

(65) Prior Publication Data

US 2002/0051968 A1 May 2, 2002

Related U.S. Application Data

(62) Division of application No. 08/934,659, filed on Sep. 22, 1997, now Pat. No. 6,391,539, which is a continuation of application No. 08/483,165, filed on Jun. 7, 1995, now Pat. No. 5,876,922, which is a continuation of application No. 08/274,159, filed on Jul. 14, 1994, now Pat. No. 5,712,092, which is a continuation of application No. 07/914,002, filed on Jul. 16, 1992, now abandoned, which is a continuation of application No. 07/758,421, filed on Sep. 3, 1991, now abandoned, which is a continuation of application No. 07/624,463, filed on Dec. 10, 1990, now abandoned, which is a continuation of application No. 07/453,218, filed on Dec. 21, 1989, now abandoned, which is a continuation of application No. 07/276,388, filed on Nov. 25, 1988, now abandoned, which is a continuation of application No. 07/159,442, filed on Feb. 18, 1988, now abandoned, which is a continuation of application No. 06/760,993, filed on Jul. 31, 1985, now abandoned.

(30) Foreign Application Priority Data

Nov. 30, 1984 (FR) .............................. 84 18369
May 9, 1985 (FR) .............................. 85 07073

(51) Int. Cl.[7] .......................................... A61K 39/395
(52) U.S. Cl. .................................. 424/130.1; 424/204.1
(58) Field of Search .......................... 424/130.1, 204.1; 435/337

(56) References Cited

U.S. PATENT DOCUMENTS

| | | | |
|---|---|---|---|
| 4,358,535 A | 11/1982 | Falkow et al. | |
| 4,419,446 A | 12/1983 | Howley et al. | |
| 4,551,270 A | 11/1985 | Danos et al. | |
| 4,748,109 A | 5/1988 | Baird | |
| 4,849,331 A | 7/1989 | Lorincz | |
| 4,849,332 A | 7/1989 | Lorincz | |
| 4,849,334 A | 7/1989 | Lorincz | |
| 4,983,728 A | 1/1991 | Herzog et al. | |
| 5,057,411 A | 10/1991 | Lancaster et al. | |
| 5,411,857 A | 5/1995 | Beaudenon et al. | |
| 5,554,538 A | 9/1996 | Cole et al. | |
| 5,744,142 A | 4/1998 | Lowy et al. | |
| 5,756,284 A | 5/1998 | Lowy et al. | |
| 5,932,412 A | 8/1999 | Dillner et al. | |

FOREIGN PATENT DOCUMENTS

| | | |
|---|---|---|
| EP | 0 192 001 | 8/1986 |
| EP | 0 425 955 | 5/1991 |
| EP | 0 477 972 | 4/1992 |
| EP | 0 489 442 | 6/1992 |
| WO | 90/02821 | 3/1990 |
| WO | 91/08312 | 6/1991 |
| WO | 91/19812 | 12/1991 |

OTHER PUBLICATIONS

Barrasso et al., "Lésions Génitales Masculines a Papillomavirus, Intérét de la Colposcopie," *Ann. Dermatol. Venereol.* (France), 113 (9): pp. 787–795 (1986).

Beaudenon et al., "A Notvel type of Human Papillomavirus Associated with Genital Neoplasias," *Nature*, 321, pp. 246–249 (1986).

Chen et al., "The primary structure and genetic organization of the bovine papillomavirus type 1 genome," *Nature*, 299, pp. 529–534 (1982).

Coggin, Jr. et al., Meeting Report, Workshop on Papillomavirus and Cancer, *Cancer Res.*, 39, pp. 545–546 (1979).

Cole et al., "Genome Organization and Nucleotide Sequence of Human Papillomavirus Type 33, Which Is Associated with Cervical Cancer," *J. Virol.*, 58(3), pp. 991–995 (1986).

Cole et al., "Nucleotide Sequence and Comparative Analysis of the Human Papillomavirus Type 18 Genome: Phylogeny of Papillomavirus and Repeated Structure of the E6 and E7 Gene Products," *J. Mol. Biol.*, 193(4), pp. 599–608 (1987).

Danos et al., EMBO, 1(2), pp. 231–236 (1982).

Durst et al., "A Papillomavirus DNA From a Cervical Carcinoma and its Prevalence in Cancer Biopsy Samples From Different Geographic Regions," *Proc. Nat'l. Acad. Sci, USA*, 80, pp. 3812–3815 (1983).

Gissman et al., "Human Papillomavirus types 6 and 11 DNA sequences in genital and laryngeal papillomas and in some cervical cancers," *Proc. Nat'l. Acad. Sci., USA*, 80, pp. 560–563 (1983).

Howley, "The Human Papillomviruses," *Arch. Pathol. Lab. Med.*, 106, pp. 429–432 (1982).

International Search Report for PCT International Patent Application No. PCT/EP 87/00158, mailed Jul. 27, 1987.

Katina et al., *EMBO*, 1(2), pp. 231–236 (1982).

(List continued on next page.)

Primary Examiner—Ali R. Salimi
(74) Attorney, Agent, or Firm—Bart W. Wise; Rhea Nersesian

(57) ABSTRACT

A purified human papillomavirus gene selected from the group consisting of E1, E6–E7, L1, and L2, wherein said human papillomavirus is selected from the group consisting of HPV-2d, HPV-10b, HPV-14a, HPV-14b, HPV-15, HPV-17a, HPV-17b, HPV-19, HPV-20, HPV-21, HPV-22, HPV-23, HPV-24, HPV-28, HPV-29, HPV-31, HPV-32, HPV-IP2 and HPV-IP4. Polypeptides encoded by these genes. The polypeptides can be used in immunogenic compositions.

1 Claim, 10 Drawing Sheets

OTHER PUBLICATIONS

Figure 1:
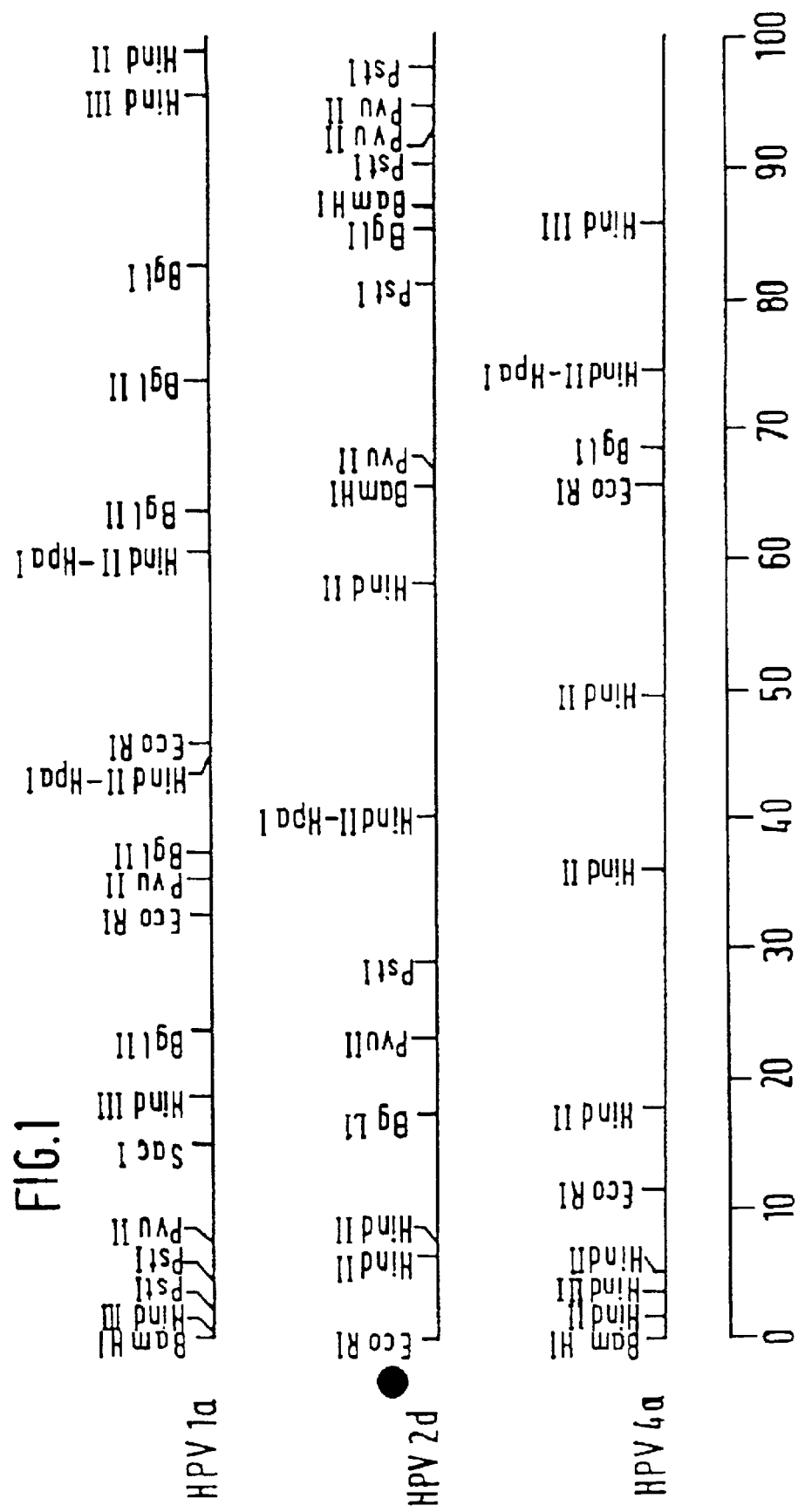

Kawashima et al., "Characterization of a New Type of Human Papillomavirus Found in a Lesion of Bowen's Disease of the Skin," *J. Virol.*, 57(2), pp. 688–692 (Feb. 1986).

Kremsdorf et al., Biochemical Characterization of Two Types of Human Papillomaviruses Associated with Epidermodysplasia Verruciformis, *J. Virol.*, 43(2), pp. 436–447 (1982).

Kremsdorf et al., "Human Papillomaviruses Associated with Epidermodysplasia Verruciformis. II. Molecular Cloning and Biochemical Characterization of Human Papillomavirus 3a, 8, 10, and 12 Genomes," *J. Virol.*, 48(2), pp. 340–351 (1983).

Kremsdorf et al., "Molecular Cloning and Characterization of the Genomes of Nine Newly Recognized Human Papillomavirus Types Associated with Epidermodysplasia Verruciformis," *J. Virol.*, 52(3), pp. 1013–1018 (1984).

Lancaster et al., "Human Papillomavirus . . . Uterine Cervix," *Chem. Abstract*, 99(3): 218, abst. 188882k, issued Dec. 5, 1983.

Orth et al., "Papillomavirus . . . infections," *Chem. Abstract*, 106(25): 348, abst. 210547s, issued Jun. 22, 1987.

Parent et al., "Les dyplasies du col utérin," *J. Gynecol. Obstet. Biol. Reprod.*, 15, pp. 941–947 (1986).

Pfister, *Rev. Biochem. Pharm.*, 99, pp. 111–181 (1983).

Pouwels et al., Cloning Vectors, A Laboratory Manual, VIII: 1–3, 5–7 (Elsevier, Amsterdam, 1985).

Rando et al., *J. Virol.*, 57, pp. 353–356 (1986).

Riov et al., *C.R. Acad. Sci.*, Ser III 14, pp. 575–580 (1984).

Schwartz et al., "DNA Sequence and Genome Organization of Genital Human Papillomavirus Type 6b," *EMBO J.*, 2(12), pp. 2341–2348 (1983).

Seedorf et al., "Human Papillomavirus Type 16 DNA: Expression of Open Reading Frames in *E. coli*," UCLA Symposium on Molecular and Cellular Biology, New Ser., vol. 32: Papillomaviruses: Molecular and Clinical Aspects, pp. 391–396 (Alan R. Liss, Inc., 1985).

Seedorf et al., "Human Papillomavirus Type 16 DNA Sequence," *Virol.*, 145, pp. 181–185 (1985).

Suggs et al., *Proc. Nat'l. Acad. Sci.*, 78, pp. 6613–6617 (1981).

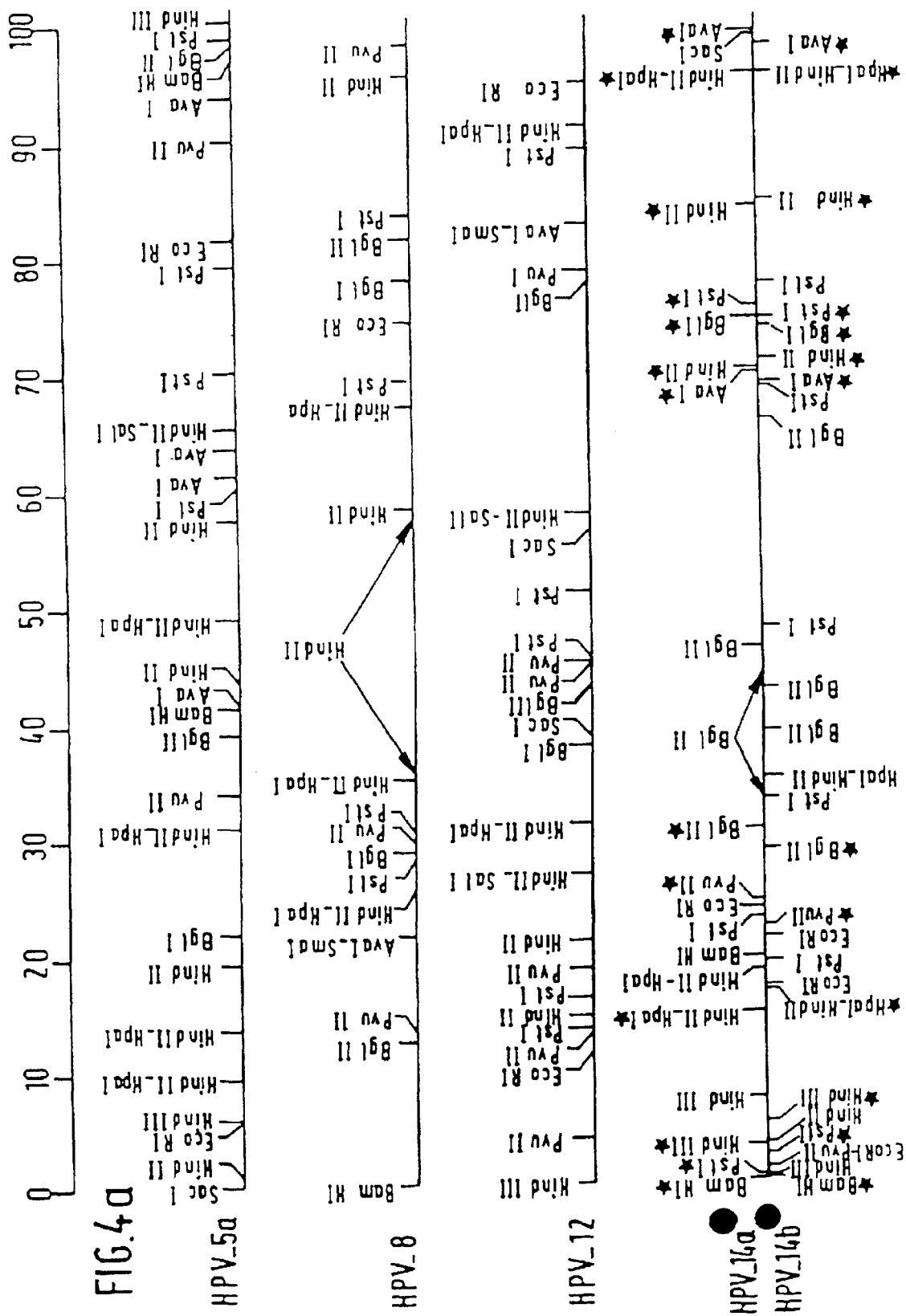

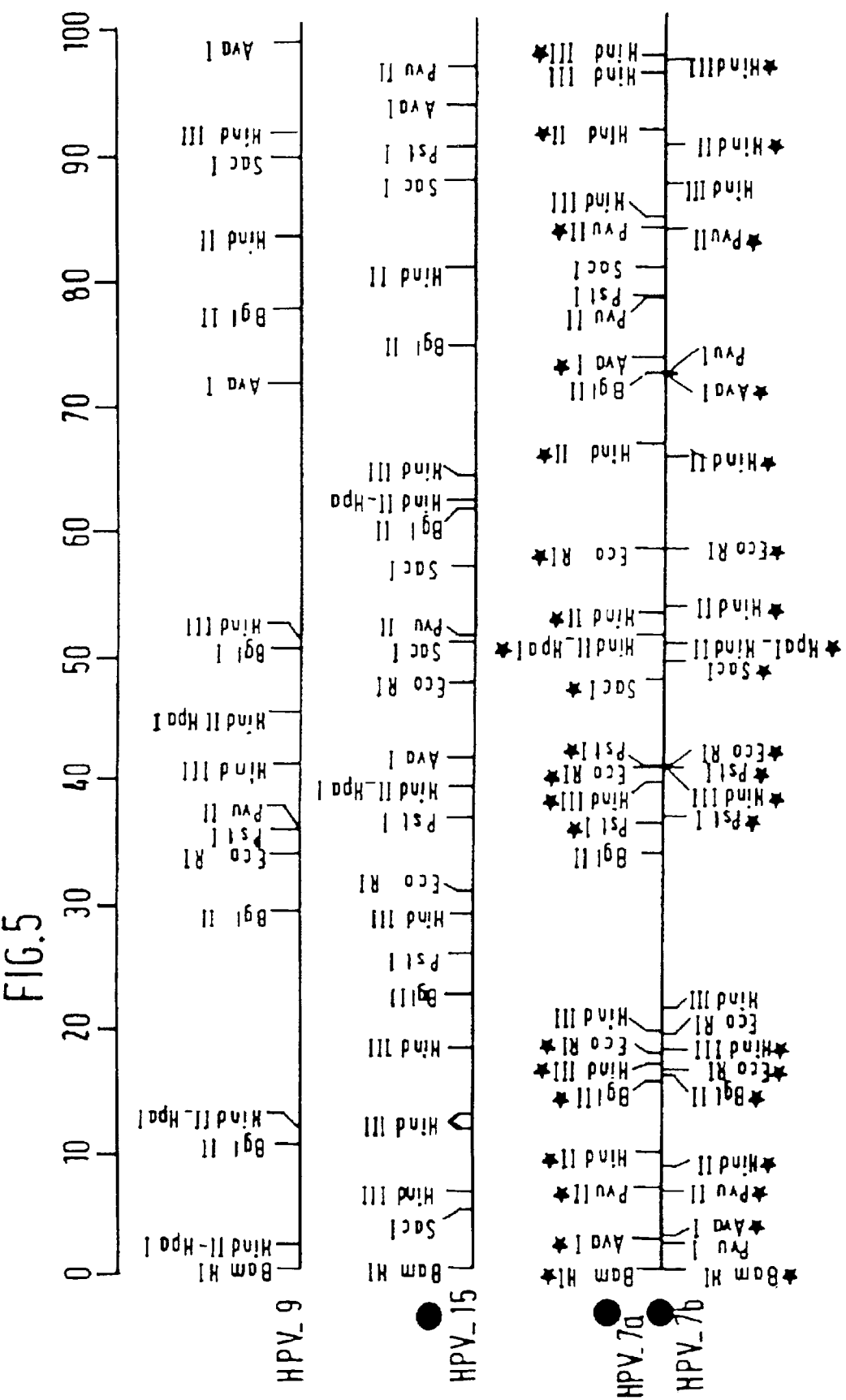

FIG. 9

HPV_IP2

- BglII (0)
- HindIII (3.8)
- PstI (8.6)
- KpnI (12.5)
- PvuII (22.5)
- PstI (23.8)
- PstI (25.7)
- HindII (26.7)
- HindIII (29.8)
- XbaI (30.2)
- KpnI (40.4)
- BglI (47.6)
- PstI (51.4)
- PvuII (73.5)
- HindII (74.3)
- AvaI-SmaI (76.9)
- HindII-NpaI (85.7)
- HindII-NpaI (89.5)
- XbaI (96.2)
- BglII (100)

HPV_IP4

- EcoRI
- PstI
- BglI
- PstI
- KpnI
- PstI
- KpnI
- PvuI
- HincII
- PstI
- HincII-HpaI
- KpnI
- BamHI
- PstI
- AvaI
- HincII
- SacI
- PstI
- HindIII
- PvuII
- HincII
- BamHI

IMMUNOGENIC COMPOSITIONS OF HUMAN PAPILLOMAVIRUS AND SERA PRODUCED THEREFROM

This is a divisional of application Ser. No. 08/934,659, filed Sep. 22, 1997, now U.S. Pat. No. 6,391,539; which is a continuation of application Ser. No. 08/483,165, filed Jun. 7, 1995, now U.S. Pat. No. 5,876,922; which is a continuation of Ser No. 08/274,159, filed Jul. 14, 1994, now U.S. Pat. No. 5,712,092; which is a continuation of Ser. No. 07/914,002, filed Jul. 16, 1992, now abandoned; which is a continuation of Ser. No. 07/758,421, filed Sep. 3, 1991, now abandoned; which is a continuation of Ser. No. 07/624,463, filed Dec. 10, 1990, now abandoned; which is a continuation of Ser. No. 07/453,218, filed Dec. 21, 1989, now abandoned; which is a continuation of Ser. No. 07/276,388, filed Nov. 25, 1988, now abandoned; which is a continuation of Ser. No. 07/159,442, filed Feb. 18, 1988, now abandoned; which his a continuation of Ser. No. 06/760,993, filed Jul. 31, 1985, now abandoned; all of which are incorporated herein by reference.

The invention concerns papillomavirus DNAs and more particularly the probes derived from these papillomaviruses, as well as the processes which use them for the in vitro diagnosis of papillomavirus infections.

The expression "papillomavirus" covers a great number of viruses having in common being considered responsible for several forms of viral infection ranging from relatively benign warts of the skin or mucous membranes to hyperplasias susceptible to degenerating into intra-epithelial neoplasms or into various forms of skin cancer. To be noted also among the papillomavirus infections are particularly the epidermodysplasias verruciformis which will sometimes be referred to hereafter by the expression "EV".

A certain number of types of papillomavirus have already been described. In the context of the present patent application, several new types and sub-types of papillomavirus will be described which have been isolated from warts or disseminated macular lesions, likely to lead to the development of precocious skin cancers in a large proportion of affected patients.

Recent studies have revealed the importance of immune factors and the manor role of human papillomaviruses (HPV), to these factors added are the role previously described in the literature of various genetic factors and actinic radiations in the pathogenesis of papillomavirus infections.

The invention is the result of observations regarding the relative behavior of a great number of newly isolated papillomaviruses whose essential genomic characteristics will be defined below.

The study of a small number of EV cases has already lead to the characterization of 6 types of HPV after molecular cloning of their genomes (KREMSDORF, D. et al. 1982, J. Virol. 43, 436–447, and KREMSDORF et al. 1983, J. Virol. 48, 340–351). These HPV have been divided into three groups as a function of the lack of cross-hybridization or very weak cross-hybridization between the genomes of the different groups. The first group includes the HPV3a and 10 which are associated with the plane warts observed in certain EV patients and in the general population ; DNA sequences related to those of HPV3a have been found in the cancer of an EV patient. The second group includes HPV5, 8 and 12, the genomes of HPV5 and 8 having been detected in the cancers of EV patients. With the exception of a kidney transplant recipient presenting an immuno-suppression, who turned out to be infected by HPV5, the virus of the two latter groups have been detected only among EV patients, most of them being infected by several viruses. It should be noted that among the 14 types of HPV currently mentioned in the literature (bibliographic references 1–5, 8, 9, 13, 14, 16, 18–20 indicated further on), four turn out to be specifically associated with EV which is a rare disease.

The labors which have led to this invention and which have permitted the isolation of a large number of new types and sub-types of papillomavirus, create the possibility of more highly refined in vitro diagnostic techniques. More particularly, the invention provides perfected techniques for papillomavirus identification, for example, of those obtained from lesions ox biopsy sections, and allows for more precise diagnoses which may also result in better prognoses with regard to the possible evolution of the lesions in question.

As a general rule, it should be noted that, despite being very different from each other, the papillomaviruses have sizes of the order of 7000–8000 base pairs. In addition, their genomes may nevertheless present certain degrees of homology. In what follows, reference will be made to evaluations of the percentage of homology between the various types and sub-types of papillomavirus, these homology percentages result from hybridization assays performed under conditions referred to as "non-stringent" or "non-strict", or under hybridization conditions called "stringent" ou "strict".

Among the papillomaviruses may be distinguished several types of papillomavirus, these may be distinguished by their percentages of homology as measured under strict or stringent conditions. Papillomaviruses which, under these conditions, present homology percentages of less than 50%, belong to different types. It may be noted in this regard, that the homology percentages between viruses of different types may even fall to zero under said strict or stringent conditions. Under these same conditions, viruses showing homology percentages of more than 50% are considered as belonging to the same type and form the different syb-types within this same type.

Hybridization assays under non-strict or non-stringent conditions implies the mutual placing into contact of DNAs derived from two viral isolates under the following conditions as described by HEILMAN, C. A. et al. 1980, J. Virol. 36, 395–407, and CROISSANT et al. 1982, C. R. Acad. Sc. Paris, 294, 81–586 (hetero-duplex molecules).

Hybridization assays under strict or stringent conditions imply the placing into mutual contact of DNAs derived from two viral isolates under the conditions described by KREMSDORF, D. Et al. (1982, J. Virol. 43, 436–447, and J. Virol. 48, 340–351) and DAVIS, R. W. et al. 1971, Methods Enzymol. 21, 413–428 (hetero-duplex molecules).

Schematically, it may be noted that those papillomaviruses belonging to one same type presenting hybridizable sequences having virtually identical nucleotide sequences over 80 to 100% of the totality of their respective lengths, these homologous sequences may be reduced to 60% or less among papillomaviruses of different types. The degree of identity or of analogy of the sequences from papillomaviruses of different types which mutually hybridize under non-strict or non-stringent conditions must obviously be less than in the case of papillomaviruses of the same type.

The study to which the inventors proceeded has shown both that the degree of genetic heterogeneousness between diverse types of papillomaviruses was greater than previously recognized and at the same time that the different types were fond often to be associated with forms or variants of infections presenting a certain degree of specificity.

The invention consequently concerns not only the DNAs susceptible to being isolated from different new papillomaviruses which have been isolated and the probes which can be partially or entirely constituted of these DNAs, but also mixtures or "cocktails" of papillomavirus types likely to be most effectively used for the diagnosis of diverse categories of infection, and of the levels of risk to the patient which accompanies the discovery of a given papillomavirus. The number of papillomavirus probes described in the present application, to which may be added, as the case may be, those constituted from the genomic DNAs of papillomaviruses which have already been previously isolated, and their associations in the specific mixtures lend greater precision to the diagnosis, notably a greater discrimination between the diverse categories of infections which may be imputed to the diverse types of papillomavirus or which may be susceptible to develop under the effect of these latter types and, within a given category of infections, to give a better prognosis of the degree of risk that these latter could be transformed to more serious disease. For example, the invention aims to provide the means permitting, in the case of infections manifesting as epidermodysplasias verruciformis, to better appreciate the degree of risk that they may evolve towards skin cancer.

In a general manner and in an attempt to simplify the following presentation, the whole genomes of the papillomaviruses will be designated by the abbreviation "HPV-DNA".

With the same aim of simplification, reference will be made to appended drawings on which figure physical restriction maps of HPV-DNAs including some from previously known papillomaviruses.

These physical maps give the positions of the fractionation sites of the various restriction endonucleases. The origin of the maps is generally constituted of the site of a single cut. The distances from this point of origin are expressed as a percentage of the total length of the genome. One unit of the map represents 1% of the length of the genome.

The invention first of all concerns most specifically each of the HPV-DNAs chosen from among the total of the DNAs having sizes ranging between 7000 and 8000 base pairs and are characterized by the restriction maps appearing in the drawings which concern more particularly HPV-DNAs obtained from papillomaviruses and which correspond to the designations HPV-2d, HPV-10b, HPV-14a, HPV-14b, HPV-15, HPV-17a, HPV-17b, HPV-19, HPV-20, HPV-21, HPV-22, HPV-23, HPV-24, HPV-28, HPV-29, HPV-31, and HPV-32, HPV-IP2 and HPV-IP4.

It goes without saying that the invention equally extends its effects to HPV-DNAs which may be considered as belonging to the same types as those Dust enumerated.

The physical maps corresponding to the HPV-DNAs of newly characterized viruses are indicated by a solid black circle on the drawings.

The invention equally concerns fragments of the preceding HPV-DNAs or capable of hybridizing with them, notably under strict conditions. Likewise it concerns those recombinant DNAs containing all or part of any of the HPV-DNAs indicated above, and more particularly recombinant DNAs containing fragments corresponding to genes E1, E6–E7, L1, and L2 respectively or again fragments containing sequences corresponding to the inter-gene regions of these said HPV-DNAs. Lastly it concerns the probes which may be constituted from these respective HPV-DNAs, and the processes of in vitro diagnosis using said probes.

Preparations of viral DNA have been selectively extracted (LUTZNER, M. A., 1983, Lancet ii:422–424) from the products of scrapings of benign lesions of six European EV patients and two South American EV patients. The HPV-DNAs were purified by equilibrium centrifugation through cesium chloride gradients and/or by sedimentation through sucrose gradients in the presence of ethidium bromide, according to the operating procedures previously described (articles by KREMSDORF, D. et al. mentioned above, and ORTH, G. et al. 1980, Cold Spring Harbor Conf. on Cell Proliferation 7:259–282). The DNA preparations were treated with restriction endonucleases and the digestion products separated by electrophoresis on agarose gels (articles by KREMSDORF et al. already mentioned). In addition, from the HPVs 5, 8 and 12 (KREMSDORF et al. articles again) and HPV-2 (HEILMAN, C. A. et al. 1980, J. Virol. 36:395–407, and ORTH, G. et al. 1980, Cold Spring Harbor conf. on Cell Proliferation 7:259–282) found in the verruca warts of one of the patients, eleven strains different from those from previously characterized types, were identified furnishing the major models for the restriction enzyme cleavage of the DNAs. The new HPV types were given a number and the sub-types of a type were given the same number followed by a letter according to the chronological order of their identification (COGGIN, J. R. et al. Cancer Res. 39:545–546). The genomes of the 11 new HPVs were cloned into *Escherichia coli* K12, strain C600 (KREMSDORF et al. article (1983) previously mentioned). The DNAs were inserted in the form of molecules of unitary length with the exception of two fragments of DNA from HPV-24 produced by endonuclease BamHI. They were inserted either into plasmid pBR322 (SUTCLIFFE, J. G., 1978, Nucleic Acids Res. 5:2721–2728), using the unique cleavage sites from AvaI, from BamHI, and from HindIII, or into a recombinant plasmid having integrated the HindIII B fragment from the DNA of HPV-5 (KREMSDORF et al. (1982) previously mentioned), which contains a unique SacI site. More particularly, the HPVs 17b and 22 were inserted in the form of DNA molecules of unitary length after splitting with an enzyme (SacI) which splits only once the DNA of HPVs and the recombinant plasmid pBR322 containing the HindIII B fragment from the DNA of HPV-5. The DNA of HPV-14a was inserted into the plasmid pBR322 in the form of a DNA molecule of unitary length after incomplete digestion of the viral DNA preparation by HINDIII, an enzyme which produces two fragments of 96.1 and 3.9% of the length of the genome. the BamHI A and B fragments of HPV-24 (having sizes corresponding to 83.1 and 16.9% respectively of the genome length) were inserted separately into plasmid pBR322.

The isolated clones and the corresponding HPV sources are listed in the appended Table I.

TABLE 1

ORIGIN OF DNAs FROM HPV CLONES

| Patient[a] | Nationality | Type of DNA from HPV | | | Other types of HPV found in the patients |
|---|---|---|---|---|---|
| | | Source[b] | cloned | Cloning[c] enzyme | |
| 1 | Polish | warts: knees | 14a 15 | Hind III Bam HI | 5 |
| 2 | French | warts: hands | 14b | Bam HI | |
| 3 | Columbian | maoules; trunk | 17a | Bam HI | 5 |
| 4 | Italian | maoules; breast | 17b 22 | Sac I Sac I | 5 |

TABLE 1-continued

ORIGIN OF DNAs FROM HPV CLONES

| Patient[a] | Nationality | Source[b] | cloned | Cloning[c] enzyme | Other types of HPV found in the patients |
|---|---|---|---|---|---|
| 5 | Dutch | maoules: back | 19 | Bam HI | 5, 8, 17a |
|   |   | maoules; breast | 24 | Bam HI |   |
| 6 | Columbian | warts: knees | 20 | Ava I | 5, 8, 24 |
| 7 | Polish | warts: knees | 21 | Bam HI | 2, 12, 17a, 20 |
| 8 | Polish | maoules; forearm | 23 | Bam HI | 5, 8, 20 |

To identify the recombinant plasmids, the electrophoretic mobilities of the digestion products of the recombinant DNAs and the non-cloned HPV-DNAs were compared after treatment with a mixture of two restriction endonucleases including the endonuclease used for the insertion of the viral sequences into the plasmid. The number and the sizes of the isolated fragments indicated that in each case the entire viral genomes were integrated. A heterogeneity of the DNA sizes was observed when non-cloned HPV-DNAs or those excised from plasmidic sequences, were analyzed by agarose gel electrophoresis (data not shown). The DNAs from HPVs 14b, 19, 20 and 21 have sizes similar to those of HPVs 3a, 5, 8 and 12 (around 7700 nucleotide pairs) (articles by KREMSDORF (1982) and ORTH (1980) already mentioned).

Figure 2:
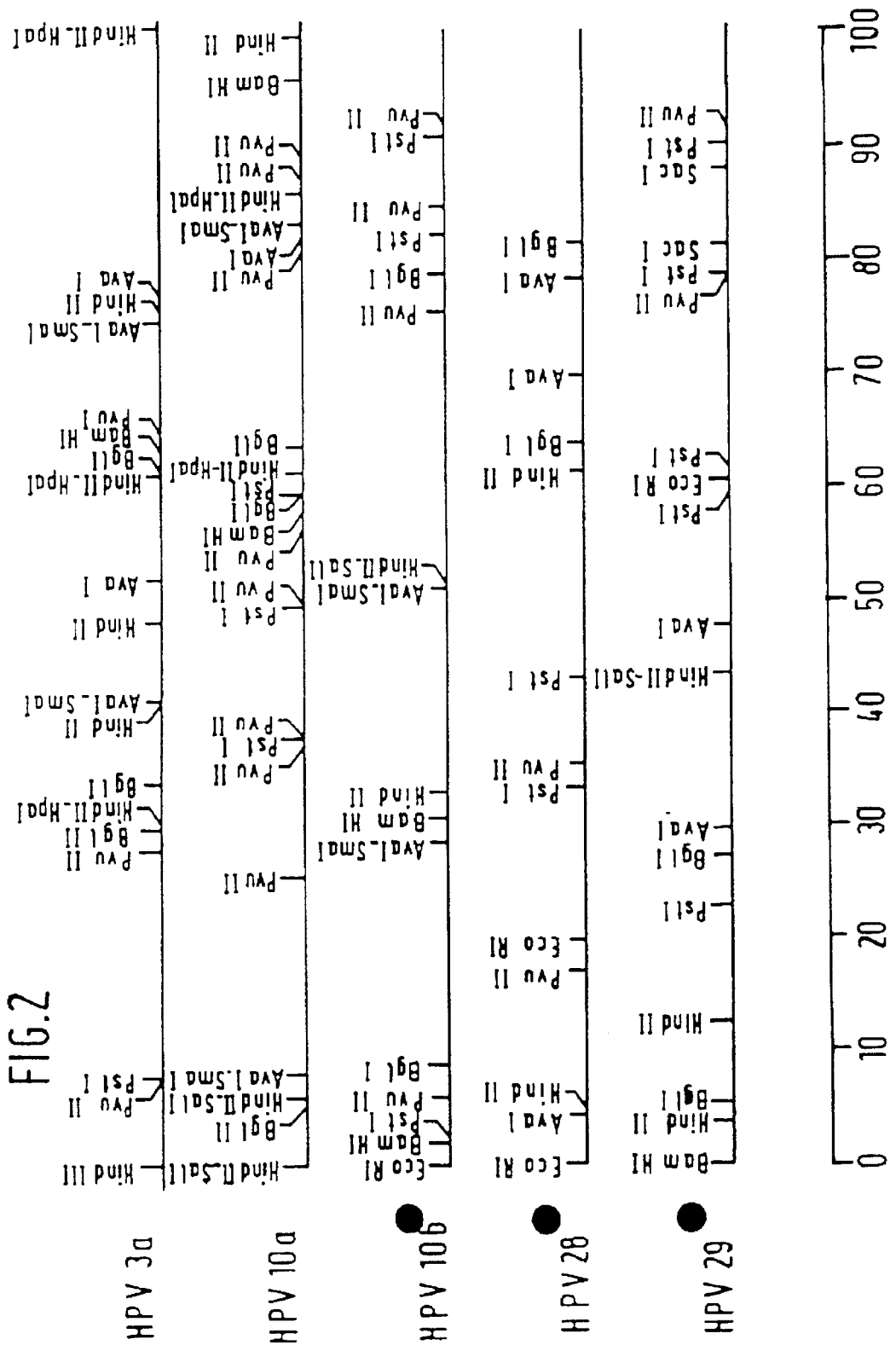
Figure 3:
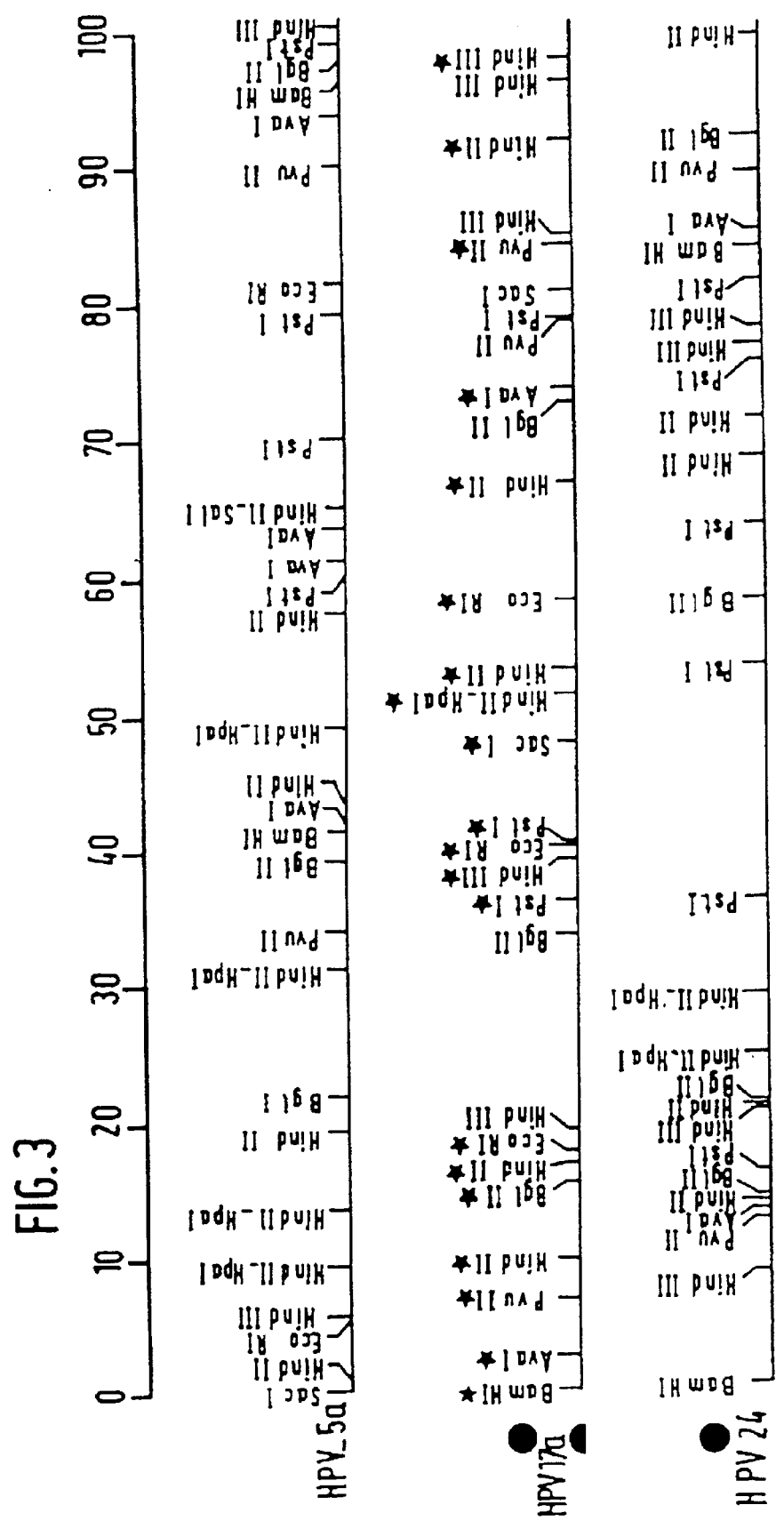
Figure 4B:
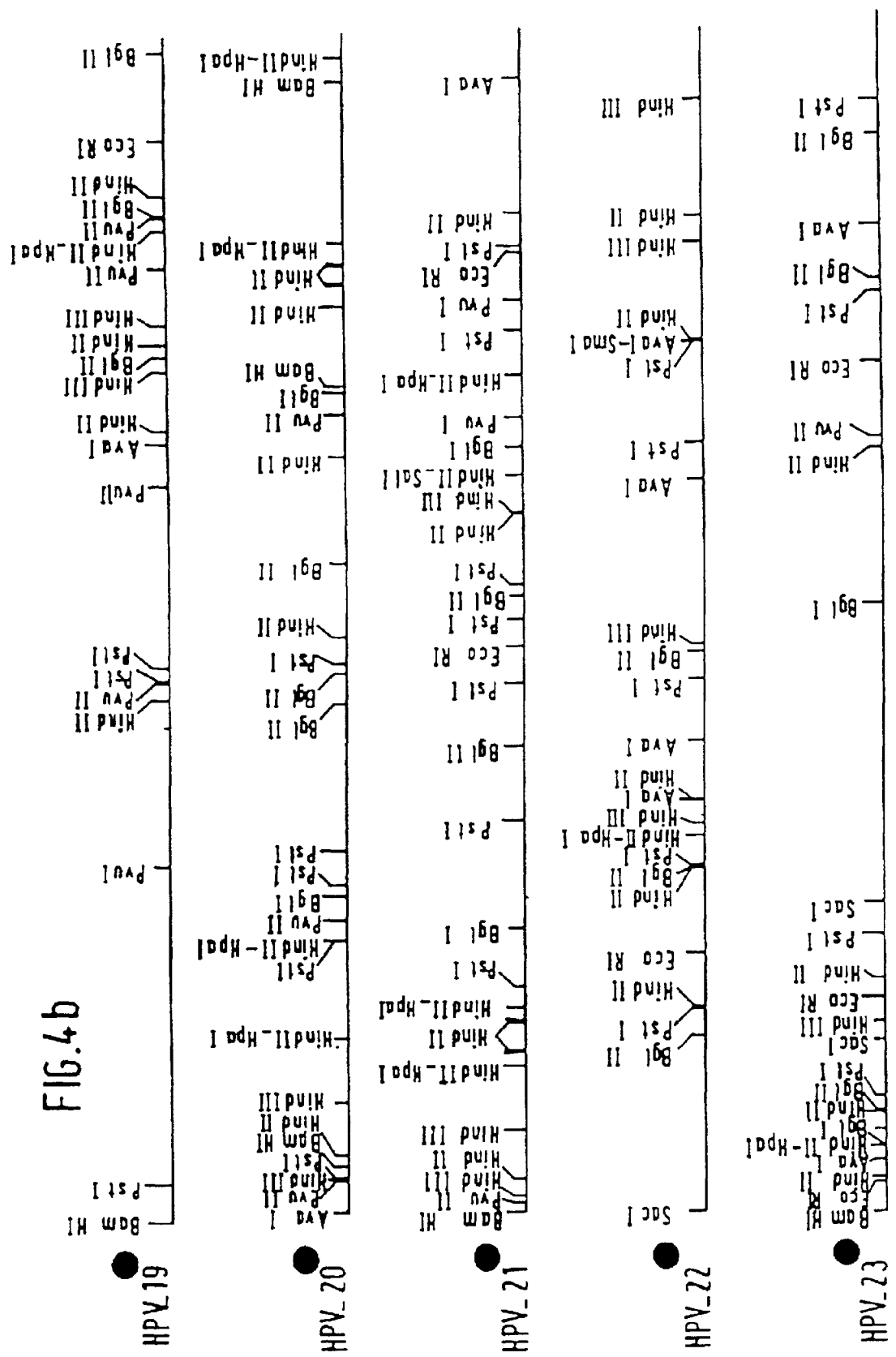
Figure 6:
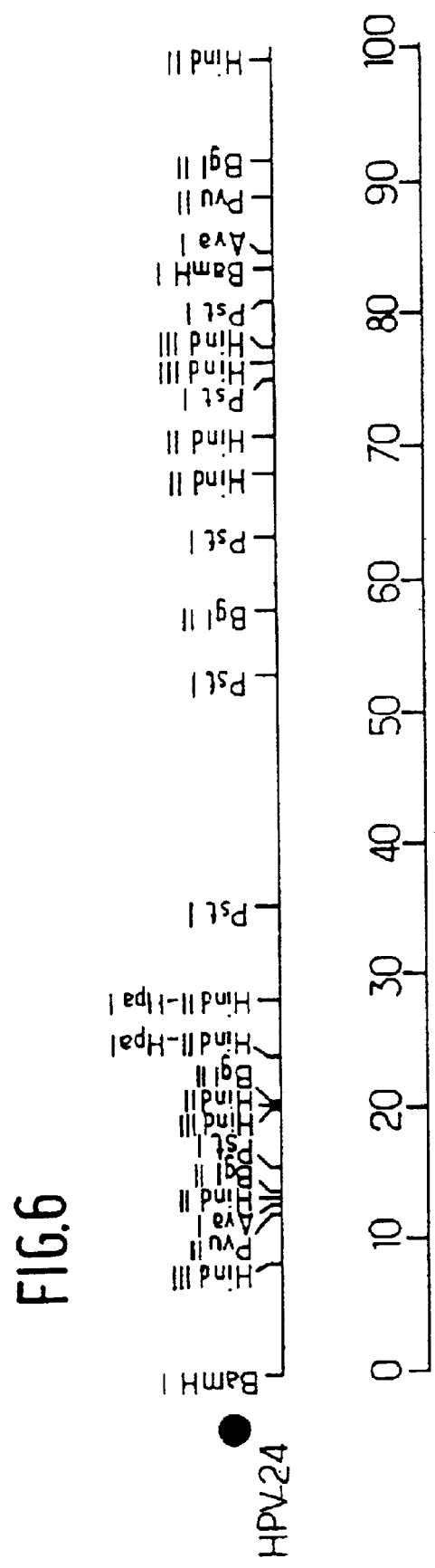
Figure 7:
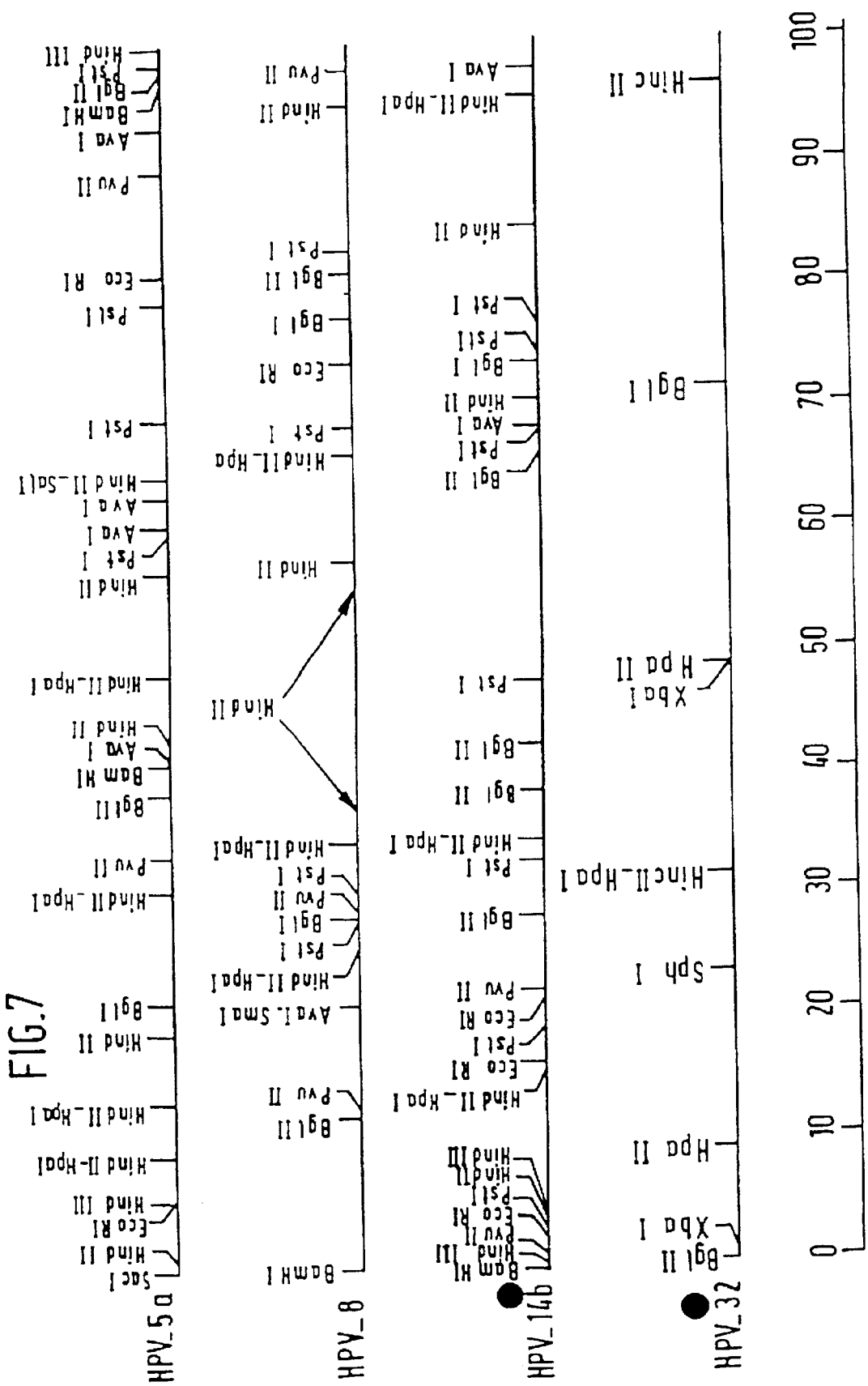
Figure 8:
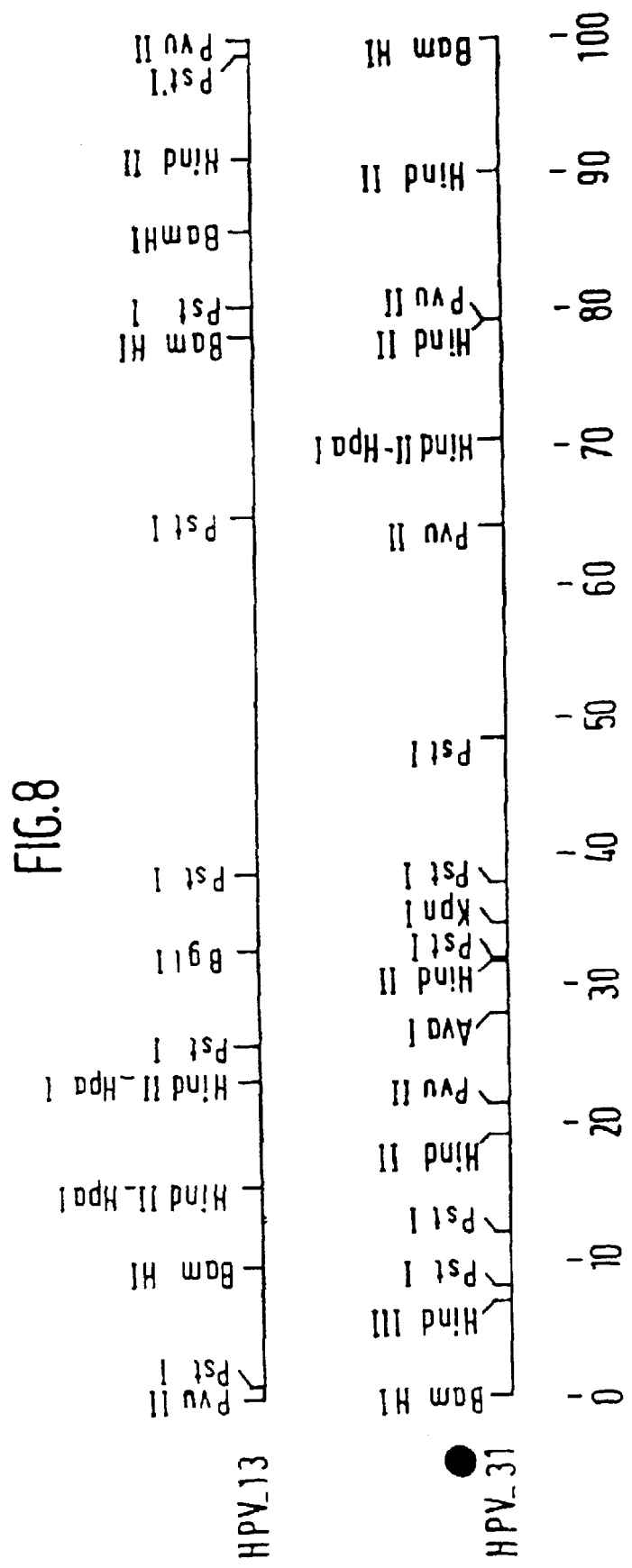

The sensitivity of cloned viral genomes to 14 restriction endonucleases was analyzed and physical maps established (FIGS. 1 through 9). The restriction maps of certain HPV-DNAs are repeated in some of the figures for reasons which will be explained further on. Between 22 and 33 cleavage sites have been localized according to the methods previously described (9). No apparent analogy could be detected between the maps with the exception of those of HPVs 14a and 14b, on the one hand (FIGS. 4a and 4b), and those of HPVs 17a and 17b, on the other (FIG. 5). Among the 21 and 31 sites localized respectively on the DNAs of the HPVs 14a and 14b, fifteen turned out to be in common when one of the two BamHI cleavage sites of the DNA of HPV-14a was aligned with the unique BamHI cleavage site of the DNA of HPV-14b. In a similar manner, 21 of the 29 cleavage sites on the DNA of HPV-17a were equally found on the DNA of HPV-17b (out of 26 sites), when the sites of the unique BamHI cleavages wer aligned.

No apparent analogy has been detected between these maps and those previously established for the HPVs associated with EV (HPVs 3a, 5, 8, 9, 10 and 12) (8, 9, 16, 18 and 20), with warts on the skin (HPVs 1, 2, 4 and 7), with lesions of the muco-cutaneous or mucous membranes (HPVs 6b, 11a, 13 and 16), with the exception of the map for HPV-14a which is closely related to the map of an HPV isolated from a Japanese male with EV (24). This latter isolate differs from HPV-14a by one additional BamHI site and one additional HINDII site, while the locations of the sites : AvaI, BamHI, BglI, EcoRI, HindII and HindIII were similar for the two viruses. Cross-hybridization experiments confirmed that these two viruses are indeed closely related.

It should be noted that some sites (those indicated by arrows) were not located. Cleavage sites differing be less than 2% of the length of the genome were considered as retained (*). Enzymes which produced no splitting were : PvuI, SalI, and SmaI for the DNA of HPVs 14a and 23; PvuI, SacI, SalI and SmaI for the DNA of HPV-14b ; BglI, PvuI, SalI and SmaI for the DNA of HPVs 15, 17a and 17b ; BglI, SacI, SalI and SmaI for the DNA of HPV-19; EcoRI, PvuI, SacI and SmaI for the DNA of HPV-20; SacI and SmaI for the DNA of HPV-21; BamHI, BglI, PvuI, PvuII and SalI for the DNA of HPV-22 BglI, EcoRI, PvuI, SacI and SmaI for the DNA of HPV-24.

The existence of sequence homologies between the DNAs of the newly characterized HPV-DNAs as well as between these and the previously characterized HPV-DNAs of EV (HPVs 3a, 5, 8, 9, 10 and 12), of HPVs associated with skin warts (HPVs 1, 2, 4 and 7), and of HPVs associated with mucous membrane lesions (HPVs 6b, 11a, 13 and 16) has been studied. Hybridization experiments by attachment onto filter paper and DNA-DNA hybridization in saturated liquid phase followed by S1 nuclease digestion were carried out under the strict or stringent conditions previously described (8, 9). In particular, the DNAs of HPVs were labeled by "nick translation" and separated by sedimentation on alkaline sucrose gradients (5 to 20%) as previously described (13). The labeled (4000 cpm) HPV-DNAs were incubated in NaCl 0.48M/EDTA 1 mM (pH 6.8) at 68 degrees C., in the presence of either calf thymus DNA (20 micrograms), or unlabeled HPV-DNA (0.20 micrograms) as previously described (8, 9). The specific activity of the HPV-DNA probes varied between $5.3 \times 10^7$ and $2 \times 10^8$ cpm/microgram. The percentage of hybridization was determined by measure of the fractions resisting the S1 nuclease. The numbers represent the values corrected for spontaneous renaturation (4 to 15%) of the probes and normalized to 100% for the homologous hybridization (75 to 95%). The abbreviation ND signifies "not determined". The relative amounts of cross-hybridization between the HPV-DNAs under the conditions indicated above are expressed as a % of hybridization between the labeled HPV-DNA and the unlabeled HPV-DNA.

TABLE 2

DEGREE OF CROSS-HYBRIDIZATION BETWEEN DNAs FROM HPV, DETERMINED BY LIQUID PHASE HYBRIDIZATION.

| Unlabeled HPV DNA | % of cf hybridization with DNA from HPV labeled with $^{32}$p | | | | | | | | | | | | | |
|---|---|---|---|---|---|---|---|---|---|---|---|---|---|---|
|   | 3a | 5 | 14a | 14b | 19 | 20 | 21 | 22 | 23 | 9 | 15 | 17a | 17b | 24 |
| 1a | 0.1 | 0.3 | 0.2 | 0.3 | 0 | 0.8 | 2.9 | 0 | 0 | 1.0 | 0.4 | 0.2 | 0 | 0 |
| 11a | 1.6 | 1.0 | 1.3 | 0 | 0.3 | 0.1 | 0.7 | 3.7 | 0 | 0.1 | 0.1 | 0.6 | 3.3 | 0 |
| 3a | 100 | 1.8 | 1.0 | 0 | 1.5 | 0.1 | 1.5 | 0 | 1.9 | 0.1 | 1.7 | 1.2 | 1.8 | 3.0 |
| 10 | 32.3 | ND | ND | 0.1 | 0 | 0.1 | 1.9 | 3.0 | ND | 0 | 1.6 | 0.1 | 2.0 | ND |

TABLE 2-continued

DEGREE OF CROSS-HYBRIDIZATION BETWEEN DNAs FROM HPV, DETERMINED BY LIQUID PHASE HYBRIDIZATION.

| Unlabeled HPV DNA | % of cf hybridization with DNA from HPV labeled with $^{32}$p | | | | | | | | | | | | | |
|---|---|---|---|---|---|---|---|---|---|---|---|---|---|---|
| | 3a | 5 | 14a | 14b | 19 | 20 | 21 | 22 | 23 | 9 | 15 | 17a | 17b | 24 |
| 5 | 0.2 | 100 | 12.1 | 12.4 | 5.8 | 9.3 | 9.4 | 10.1 | 5.0 | 4.3 | 0.7 | 3.6 | 0 | 2.4 |
| 8 | 1.1 | 15.7 | 9.9 | 13.4 | 8.5 | 5.6 | 5.0 | 7.1 | 5.0 | 3.5 | 1.5 | 3.2 | 3.8 | 0.1 |
| 12 | 0.1 | 19.3 | 9.2 | 12.5 | 5.3 | 0.6 | 9.3 | 11.7 | 4.0 | 3.6 | 1.2 | 0.1 | 1.9 | 0 |
| 14a | 0.2 | 13.2 | 100 | 00.0 | 14.6 | 12.4 | 32.9 | 10.1 | 24.6 | 3.0 | 2.2 | 2.4 | 4.1 | ND |
| 14b | ND | 10.5 | 94.1 | 100 | 9.3 | 20.4 | 35.4 | 9.5 | 20.2 | 0 | 0 | 0 | 0 | 0 |
| 19 | ND | 7.2 | 21.4 | 20.6 | 100 | 7.6 | 0.0 | 15.5 | 27.7 | 0 | 0 | 0 | 2.2 | 1.0 |
| 20 | ND | 9.9 | 28.8 | 37.9 | 6.2 | 100 | 25.4 | 13.7 | 14.1 | 0 | 0 | 2.1 | 0 | 3.6 |
| 21 | ND | 10.5 | 38.7 | 40.5 | 6.4 | 37.5 | 100 | 9.8 | 10.6 | 0.1 | 0 | 2.5 | 0.3 | 0 |
| 22 | ND | 7.2 | 7.4 | ND | 17.3 | 7.2 | 10.0 | 100 | 17.9 | 0 | 0 | 0.1 | 0.1 | 0 |
| 23 | ND | ND | ND | ND | ND | ND | ND | 21.2 | 100 | 0 | 0.5 | 0 | 0 | 0.1 |
| 9 | 0.4 | 3.1 | 0.5 | 1.2 | 0 | 2.0 | 1.0 | 0 | 0 | 100 | 5.5 | 6.3 | 5.4 | 0 |
| 15 | 0.4 | 3.3 | 2.1 | 3.3 | 0 | 0.1 | 0.0 | 0 | 0 | 7.8 | 100 | 22.5 | 21.6 | 0 |
| 17a | 0.7 | 1.2 | 1.4 | 2.0 | 0 | 0.1 | 0.1 | 0.8 | 1.4 | 7.6 | 19.5 | 100 | 92.7 | 0 |
| 17b | ND | ND | ND | 1.4 | 0 | 0.3 | 3.4 | ND | ND | ND | ND | 86.3 | 100 | ND |
| 24 | ND | ND | 0.1 | 2.6 | ND | ND | ND | 0.8 | 0 | 0.2 | 0 | 1.1 | 1.1 | 100 |

ND = not determined.

The absence or near absence of cross-hybridization between the genomes of HPVs 1, 2, 4, 6b, 7 and 11, and the HPV-DNAs of 32 P labeled newly cloned EV, or between unlabeled HPV-DNAs of EV and probes specific to HPVs 13, 16 and 18 is to be noted. In a similar manner, almost no cross-hybridization has been detected between the DNAs of HPVs 14a, 14b, 15, 17a, 17b, 19, 20, 21, 22, 23 and 24, and the DNAs of HPVs 1a and 11a by saturation reassociation (Table 2). The DNAs of newly cloned HPVs showed little or no cross-hybridization or showed less than 50% cross-hybridization between each other and with the genomes of other HPVs associated with EV (HPVs 3a, 5, 8, 9, 10 and 12) with the exception of HPVs 14a and 14b on the one hand, and HPVs 17a and 17b on the other, which showed strong cross-hybridization. These observations justify the classification of the new viruses into nine new types (HPVs 14, 15, 17, 19, 20, 21, 22, 23 and 24) plus two sub-types of types 14 (HPV-14a and 14b) and 17 (HPV-17a and 17b).

Likewise, the different HPVs have been classed into groups based on their homologies (or lack of them) of sequences under the strict conditions of molecular hybridization. These groups, designated by the letters A to H, are listed in Table 3 which is appended. This Table mentions the diseases which have been diagnosed among the carriers of these HPVs (separately or in combination) and their oncogenic potential.

TABLE 1

CLASSIFICATION OF HPVs WHICH ARE THE OBJECT OF THIS PATENT APPLICATION, AS A FUNCTION OF THE DEGREE OF HOMOLOGY OF THEIR NUCLEOTIDE SEQUENCES AS DETERMINED BY MOLECULAR HYBRIDIZATION UNDER STRICT CONDITIONS

| Group[1] | HPV types[2] | Homologies within the group | Associated diseases | Oncogenic potential | Probe mixture |
|---|---|---|---|---|---|
| A | 1 | | Myrcemies | very weak | 1 |
| B | 2 | | Verruca warts | weak | 1 |
| C | 3, 10, 28*, 29* | 14 to 38% | Plane warts Intermediary warts Actinic keratoses Bowen's disease | moderate; a related virus, associated | 2 |

TABLE 1-continued

CLASSIFICATION OF HPVs WHICH ARE THE OBJECT OF THIS PATENT APPLICATION, AS A FUNCTION OF THE DEGREE OF HOMOLOGY OF THEIR NUCLEOTIDE SEQUENCES AS DETERMINED BY MOLECULAR HYBRIDIZATION UNDER STRICT CONDITIONS

| Group[1] | HPV types[2] | Homologies within the group | Associated diseases | Oncogenic potential | Probe mixture |
|---|---|---|---|---|---|
| D | 4 | | Verruca warts | with intra-epithelial neoplasms and evolving skin cancers very weak | 1 |
| E | 5, 8, 12, 14* 19*, 20*, 21*, 22*, 23* | 4 to 18% | Epidermodysplasia verruciformis Actinic keratoses Bowen's disease Skin cancers | HPVs 5, 8 and 14 associated with cancers from E.V.; an related virus, associated with intra-epithelial neoplasms and evolving skin cancers | 3, 4, 7 |
| F | 9, 15, 17*, | 6 to 23% | Epidermodysplasia verruciformis | | 5 |
| G | 24* | | Epidermodysplasia verruciformis | | 6 |
| H | 13, 31* | | Oral epithelial hyperplasia; oral leucoplasias | | 8 |
| I | 32* | | Bowen's disease | Intra-epithelial neoplasm and skin cancers | 7, 9 |

[1] Genomes of HPV types belonging to different groups, generally present no detectable sequence homology under strict molecular hybridization conditions. Genomes of HPV types belonging to the same group show less than 50% sequence homology.
[2] The new HPV types are indicated by an asterisk.

The DNAs of HPVs 5, 8, 12, 14, 19, 20, 21, 22 and 23 show between them levels of cross-hybridization (group homologies) varying from 5 to 38% and show no notable cross-hybridization (4 to 13%) except with the DNAs of HPVs 5, 8 and 12. These viruses thus form a part of a group of HPVs of EV previously defined (9).

Likewise, the DNAs of HPVs 9, 15 and 17 which show between them cross-hybridization of around 20% and cross-hybridization of around 6% with the DNA of HPV-9, equally belong to a group of EV HPVs previously described (9). The HPVs of types 13 and 31 may be considered as belonging to one same group. And last, the HPVs of types 1, 2, 4, 24 and 32 which show almost no homology with the genomes of the other HPVS, are considered as forming the first members of other groups which are distinct from each other and from the previous groups.

The invention concerns still more particularly the DNA fragments derived from the above described HPV-DNAs, and especially those corresponding to genes E6–E7, E1, L2, L1 and to their inter-gene regions. The relative positions and lengths of these various fragments in relation to the sites taken as origins (FIGS. 1 to 9) are indicated in Table 4 appended.

TABLE 4

PUTATIVE LOCATION OF THE PRINCIPAL GENES AND OF THE INTERGENE REGIONS ON THE PHYSICAL HAPS OF THE HPV GENOMES.

| Type of HPV | Co-ordinates of the 5' and 3' ends, corresponding to genes | | | | Intergene region |
|---|---|---|---|---|---|
| | E6–E7 | E1 | L2 | L1 | |
| 1 | 44–34.5 | 35–11 | 95–75.5 | 16.5–56 | 56–44.5 |
| 3 | 18.5–9 | 9.5–85.5 | 69.5–50 | 51–30.5 | 30.5–19 |
| 5 | 6.5–97 | 91.5–73.5 | 57.5–30 | 39–18.5 | 18.5–7 |
| 8 | 63–53.5 | 54–30 | 14–94.5 | 95.5–75 | 75–63.5 |
| 9 | 42–32.5 | 33–9 | 93–73.5 | 74.5–54 | 54–42.5 |
| 10a | 49–39.5 | 40–16 | 0–00.5 | 81.5–61 | 61–49.5 |
| 10b | 93–83.5 | 84–60 | 44–24.5 | 25.5–5 | 5–93.5 |
| 12 | 23.5–14 | 14.5–90.5 | 74.5–55 | 56–35.5 | 35.5–24 |
| 14 | 8.5–99 | 99.5–75.5 | 59.5–40 | 41–20.5 | 20.5–9 |
| 15 | 39.5–30 | 30.5–6.5 | 90.5–71 | 72–51.5 | 51.5–40 |
| 17 | 46–36.5 | 31–13 | 97–77.5 | 70.5–58 | 58–46.5 |
| 24 | 24.5–15 | 15.5–91.5 | 75.5–56 | 57–36.5 | 36.5–25 |
| 28 | 47.5–38 | 38.5–14.5 | 98.5–79 | 80–59.5 | 59.5–48 |
| 29 | 89.5–80 | 80.5–56.5 | 40.5–21 | 22–1.5 | 1.5–90 |
| 31 | 89–70.5 | 80–53.5 | 33.5–15.5 | 11.5–96.5 | 96.5–92.5 |

The localization of genes on the genome of HPV-1 has been deduced from the nucleotide sequence of this genome (patent of O. DANOS, M. KATINKA and M. YANIV). The physical maps of the genomes of the HPVs 3, 5, 8, 9, 10a, 12, 14, 15, 17 and 24 have been aligned relative to the physical map and the gene map of HPV-1, and that of HPV-31 relative to the physical map and gene map of HPV-6b (E. SCHWARZ and al, EMBO J., 1983, 2, 2341–2348), after electron microscope analysis of the hetero-duplex molecules formed under strict conditions (Tm −29 degrees C.) or less strict (Tm −40 degrees C.) of hybridization. The physical maps of HPVS 10b, 28 and 29 were lined up against the pysical maps of HPVs 3a and 10a after juxtaposition of the retained restriction enzyme sites.

The values of the co-ordinates shown in table 4 give the position, on the physical amps presented in FIGS. 1–9, the 5' and 3' ends of th genome segments homologous with the genes E6 and E7, E1, L2 and L1 and with the inter-gene region relative to the genome of HPV-1a, or, in the case of HPV-31, relative to the genome of HPV-6b.

The inter-gene region (which includes the elements of regulation) and the adjacent E6 and E7 genes (corresponding probably to the major genes of transformation expressed in tumors) show no sequence homology detectable by electron microscope analysis of the hetero-duplex molecules formed (under non-strict hybridization conditions) between the genomes of HPV types belonging to different groups, or formed (under strict hybridization conditions) between the genomes of most of the HPV types belonging to the same group. Gene E1 (implicated principally in the replication of viral DNA) and gene L1 (coding for a major protein of the viral capsid bearing the virion's principal antigenic determinants) show sequence homologies detectable by the analysis of hetero-duplexes formed (under non-strict hybridization conditions) between the genomes of HPV types belonging to different groups, or (under strict conditions) between the genomes of HPVs belonging to same group.

Probes prepared from recombinant plasmids which include the E1 and L1 regions could theoretically permit the detection of the greatest number of HPV types by molecular hybridization experiments under strict or non-strict conditions according to the case. Probes prepated from recombinant plasmids which include the inter-gene region and the genes E6 and E7 permit the specific detection of one HPV type or related HPV types.

The L2 region (coding for a minor constituent of the viral capsid) shows a variable degree of conservation of nucleotide sequences among the different HPV types.

In what follows, the conditions under which the viruses HPV-IP2 and HPV-IP4 have been isolated will be described more precisely, as will the conditions under which the HPV-DNAs from these viruses were obtained.

Molecular cloning and characterization of a new type of HPV associated with neoplasms and genital cancers (HPV-IP2).

A new type of HPV has been demonstrated in the DNA extracted from a cancer of the cervix, by hybridization under non-strict conditions with a radioactive probe specific to HPV type 16. No cross-hybridization was detectable when the hybridization was carried out under the strict conditions of hybridization. A study of the sensitivity of the DNA of this HPV to a number of restriction enzymes has shown that the enzyme BglII cut once the viral DNA. After digestion of the DNA extracted from the tumor, by the endonuclease BglII, the fraction containing the DNA molecules of 8kb (size of a genome of papillomavirus) were purified by centrifugation through a sucrose gradient. The 8kb molecules were inserted, at the BglII site, into a vector constituted of the plasmid PL15.5 (which includes a single cut site by BglII and by BamHI) which was inserted by it's BamHI site into the DNA of the bacteriophage lambda L47.1. After encapsidation of the recombinant DNA and infection of the host bacteria *Escherichia coli* strain (LA101), the areas of lysis corresponding to recombinant phages were detected by hybridization of the replicated infected bacterial cultures, with DNA from radioactive HPV-16, under non-strict conditions. Several recombinant bacteriophages, containing the totality of the viral sequences, have been isolated: the cutting of the phagic DNA by the insertion enzyme BglII results in a fragment of 8kb hybridizing with the HPV-16 under non-strict conditions; the cutting of the DNA of the recombinant phages and of the DNA of the tumor of origin by a mixture of the enzymes BglII and PstI leads to the same 5 fragments, the total molecular weight of which is equal to the size of a genome of the papillomaviruses. The DNA of the new HPV was excised from the DNA of the recombinant bacteriophages, purified by electro-elution, and recloned in the plasmid PL15.5. A restriction map of the viral DNA has been established based on the sensitivity of this DNA to 18 restriction endonucleases, permitting 21 cut sites to be localized (FIG. 9). The map thus established is different from the map of the genomes of HPVs identified up til now. The sequence homology between the DNA of the new HPV and the DNA of the HPVs identified up til now were analyzed by molecular hybridization experiments on culture replicas under strict conditions. The homology detected was always less than 5% the greatest homology was detected with the genome of HPV-16. The new virus characterized from a cervical cancer therefore constitutes a new type of HPV, provisionally called HPV-IP2.

The analysis, by electron microscopy, of the heteroduplex molecules formed under different conditions between the DNA of HPV-IP2 and the DNA of HPV-1 permitted the alignment of the physical maps of these two genomes and the definition of the theoretical positions of the different genes of the DNA of HPV-IP2.

PUTATIVE POSITIONS OF THE PRINCIPAL GENES AND OF THE INTER-GENE REGION OF THE HPV-IP2 ON THE MAP OF THIS GENOME.

| Co-ordinates of the ends: | 5' and | 3' |
|---|---|---|
| E6–E7 | 62 | 71.5 |
| E1 | 71 | 95 |
| E2 | 95.5 | 11.5 |
| L2 | 11 | 30.5 |
| L1 | 31.5 | 52. |
| Inter-gene region | 52 | 63.5 |

The use of radio-active probes prepated from the DNA of purified HPV-IP2 has permitted the determination of the pathogenic power of these viruses. The DNA of HPV-IP2 was found in one case of Bewenoid papula of the external genital organs, out of 14 cases studied ; in two cases out of 51 of invasive cervical cancer studied; and in 1 case of cervical intra-epithelial neoplasm out of 28 studied. Thus HPV-IP2 constitutes a genito-tropic type of HPV with oncogenic potential whose frequency is a little less than that of HPV-18, and much less than that of HPV-16. It is necessary to include it in any mixture of HPV-DNAs intended for the preparation of molecular probes for the diagnosis of, or screening for, the types of HPVs presenting a risk of the development of genital neoplasms and, in particular, of cervical cancer.

Molecular cloning and characterization of a new type of HPV associated with Pre-cancerous lesions of the skin (HPV-IP4 1.

A new type of HPV has been found in the DNA extracted from the biopsy of an actinic keratosis, a pre-cancerous skin lesion, by molecular hybridization under strict conditions, with a mixture containing radioactive probes specific for HPV types 5, 8 and 14. No cross-hybridization was detected when the hybridization was carried out with probes specific to types 1, 2, 3, 7, 10, 13, 16, 18, 28, IP-1 (previously named HPV-31), IP-2 and IP-3 (previously named HPV-32).

A study of the sensitivity of this HPV to several restriction enzymes has shown that the enzyme EcoRI cuts the viral DNA once. After digestion of the DNA extracted from the biopsy by the endonuclease EcoRI, the fraction which contains the molecules of DNA of Bkb (size of a genome of papillomavirus) was purified by centrifugatin through a sucrose gradient). The 8kb molecules were inserted, by the EcoRI site, into the DNA of the bacteriophage lambda gt wes. lambda B. After encapsidation of the recombinant DNA and infection of the host bacteria (Escherichia coli, strain LA101), the areas of lysis corresponding to the recombinant phages were detected by hybridization of the replicated infected bacterial cultures, with a radio-active mixture of DNAs from the HPVs 8 and 14 under non-strict conditions. Several recombinant bacteriophages, containing the totality of the viral sequences, have been isolated: the cutting of the phagic DNA by the insertion enzyme EcoRI results in an 8kb fragment hybridizing with the probe specific to HPVs 5, 8 and 14 under non-strict conditions ; the cutting of the DNA of the recombinant phages and the DNA of the original lesion by a mixture of the enzymes EcoRI and PstI results in the same 6 fragments, the total molecular weight of which equals the size of a genome of the papillomaviruses. The DNA of the new HPV was excised from the DNA of a recombinant bacteriophage, purified by electro-elution, and recloned into the plasmid pSP65. A restriction map of the viral DNA was established from the sensitivity of this DNA to 15 restriction endonucleases, which has permitted the localization of 23 cut sites (FIG. 9). The map thus established is different from the map of the genomes of HPVs identified up til now. The sequence homology between the DNA of the new HPV and the DNAs of the HPVs identified up to now has been analyzed by molecular hybridization experiments on cultures under strict conditions. A homology, less than 50%, has been detected between the DNA of the new HPV and the DNA of certain types of HPVs previously identified in the lesions of epidermoplasia verruciformis (HPVs 5, 8, 12, 14, 19, 20, 21 and 25), but no homology was detected with other HPV types. The new virus characterized from an actinic keratosis thus constitutes a new type of HPV provisionally named HPV-IP4.

The use of a radioactive probe prepared from the DNA of purified HPV-IP4 has permitted the demonstration of HPV-IP4 in 42% of the 17 patients studied having epidermodysplasia verruciformis and in x out of y biopsies of actinic keratosis analyzed. Because of its great frequency among patients of EV, a disease characterized by the frequent development of skin cancers, and because of its association with a fraction of the lesions of actinic keratosis considered as precursors of spinocellular cancers of the skin. HPV-IP4 constitues a type of dermo-tropic HPV with oncogenic potential. It is necessary to incorporate it into any mixture of HPV-DNAs intended for the preparation of molecular probes for the diagnosis or screening of HPV types constituting a risk of the development of cancerous or precancerous skin lesions.

The invention still more particularly concerns the mixtures or cocktails of different HPV-DNAs (or probes containing these HPV-DNAs or sequences from them), susceptible to being used in combination to create means for the global diagnosis of the different forms of papillomavirus infections, possibly for use in the prognosis of the possible evolution of the infection. The preferred mixtures conforming to the invention are identified in Table 5 appended.

TABLE 5

CHARACTERISTICS OF THE HPV-DNA MIXTURES USEABLE FOR THE DETECTION OF PAPILLOMAVIRUS INFECTIONS

| Designation of the mixtures | Constitution[1] | Diagnosable diseases |
|---|---|---|
| 1 | 1, 2d*, 4 | Skin or mucous membrane warts (especially verruca and plantar warts). Differential diagnosis of epidermodysplasia verruciformis. |
| 2 | 3, 10a, 10b*, 28*, 29* | Plane warts or intermediary skin or mucous membrane warts. Intra-epithelial neoplasms and skin cancers. Differential diagnosis of epidermodysplasia verruciformis. |

TABLE 5-continued

CHARACTERISTICS OF THE HPV-DNA MIXTURES USEABLE
FOR THE DETECTION OF PAPILLOMAVIRUS INFECTIONS

| Designation of the mixtures | Constitution[1] | Diagnosable diseases |
|---|---|---|
| 3 | 5, 17a*, 24* | Epidermodysplasia verruciformis. Intra-epithelial neo-plasms and skin cancers. |
| 4 | 5, 8, 12, 14a*, 14b*, 19*, 20*, 21*, 22* 23* | Epidermodysplasia verruciformis. |
| 5 | 9, 15*, 17a*, 17b* | Epidermudysplasia verruciformis. |
| 6 | 24* | Epidermodysplasia verruciformis. |
| 7 | 5, 8, 14b*, 32* | Skin cancers from epidermodysplasia verruciformis. Intra-epithelial neoplasias and skin cancers. |
| 8 | 13, 31* | Oral epithelial hyperplasia; differential diagnosis of oral epithelial neoplasms. |
| 9 | 32* | Intra-epithelial neoplasus and skin cancers. |

[1]The new types of HPV are indicated by an asterisk.

This Table also indicates the natures of the affections susceptible to being more particularly diagnosed by the use of the mixtures figuring on the left side of the table. It should be noted that the grouping of the restriction maps in the appended FIGS. 1 to 9 conform to the groupings given in the column headed "Composition" in table 5. This is equally the reason why some of the probes are reproduced several times in the different figures of the appended drawings.

Each of these mixtures may again be defined as including at least one of the new probes according to the invention. In other words, the diagnostic compositions according to the invention may be defined as containing :

| 1) | at least the DNA of HPV-2d, |
| 2) | at least the DNA of one of the HPVs 10b, 28 and/or 29, |
| 3) | at least the DNA of one of the HPVs 17 and/or 24, |
| 4) | at least the DNA of one of the HPVs 14, 15, 17, 19, 20, 21, 22 and/or 23, |
| 5) | at least the DNA of one of the HPVs 15 and/or 17, |
| 6) | the DNA of HPV-24, |
| 7) | the DNA of HPVs 14 and 32, |
| 8) | the DNA of HPV-31, |
| 9) | the DNA of HPV-32, | it being understood that the DNAs of the nine groups are chosen in such a manner as to in all circumstances be different from each other.

In view of the great diversity of HPVs susceptible of being isolated from the different forms of warts or other skin or mucous membrane lesions, it is nevertheless preferable, for the diagnosis of each type of disease mentioned in the table, to use mixtures containing more than one or two HPV-DNAs, since it has been recognized that other HPV-DNAs may equally intervene in the same type of affection. The diagnosis of the nature of the infection and its possible evolution will be that much more effective as the number of probes used is increased. In addition, hybridization assays carried out with the different mixtures of probes will allow differential diagnoses with an equivalently greater degree of probability, of the disease from which the patient suffers.

In Table 5, only probes formed from HPV-DNAs isolated in the laboratories of the inventors, have been mentioned. It goes without saying that, because of the preceding, the different mixtures may be improved by the addition of other HPV-DNAs obtained through the works of other laboratories, once such are found from the various afflictions of the same kind presented by patients. For example, mixture 7 can only be improved by the addition of any other HPV-DNAs encountered in epidermodysplasias verruciformis with the risk of transformation into intra-epithelial neoplasms and skin cancers. Note that in table 5, certain of the mixtures are presented as being characteristic to the diagnosis of the same diseases. It should nevertheless be recognized that the different mixtures make a distinction between those infections implying little risk of cancerization, and those bearing a high risk of it. For example, the hybridization of a viral preparation derived from a patient submitted for diagnosis, with mixture 7, suggests a greater risk of evolution to skin cancer than if the sample had hybridized to a greater degree with the probes of mixture 3.

Likewise, the cases of EV detected by mixture 5 implies a greater risk of cancerization than those cases detected with mixture 6. Mixture 4 will discern EV cases having an even higher risk than those detected by mixture 5.

In the following is described other mixtures or cocktails of different HPV-DNAs (or probes containing these HPV-DNAs or sequences of them), susceptible of being used in combination for the realization of global diagnoses of the different forms of papillomavirus infections, perhaps for the purposes of determining a prognosis of the possible evolution of the affliction.

The preferred mixtures conforming to the invention are identified in the aforesaid table 5.

The aforesaid table equally indicates the natures of the affections susceptible of being more particularly diagnosed by the use of the mixtures figuring on the left side of the table. It is to be recalled that the restriction maps of other HPV-DNAs identified in the preceding table are contained in the FIGS. 1 through 9.

It should be noted that HPV-IP2 may be considered as particularly representative of the probes useable for the detection of the risk of developing genital neoplasms and, in particular, cervical cancers.

The invention therefore concerns more particularly yet the "kits" for diagnosis including at least 10 groups figuring in the groups numbered 1 to 10 in the table under the heading "Designation of the mixtures".

In the preceding, what was primarily under consideration was the use, as probes, of whole, cloned HPV-DNAs. These, however, could be replaced by cloned fragments of these different DNAs, notably by the genes E1 or L1 and by the genes E6–E7.

The basic principal of in vitro detections of HPV-DNAs will naturally involve hybridizations operated under strict or less strict conditions. A procedural example follows, it being of course understood that the diagnostic assays described should in no way be considered as limiting the conditions of use of the probes or mixtures of the probes according to the invention.

The object of examinations involving probes prepared from mixtures of DNAs from cloned HPVs is to reveal an HPV and identify the type of HPV in a biopsy, in cells obtained by scraping a lesion, or in biopsy sections fixed with Carnoy's mixture (ethanol, chloroform, acetic acid 6:3:1) and included in paraffin. The examination requires the prior extraction of the DNA from the samples according to methods the principal of which is known and involves the analysis of this DNA by molecular hybridization under strict or less strict conditions with the aid of radioactive probes (labeled with $^{32}$p or $^{35}$S) prepared from mixtures of HPV-DNAs. In general, each examination requires the use of several mixtures of probes.

Several hybridization methods may be used. For example, the spot hybridization method includes, after denaturation of the DNA, the deposition of an aliquot of the DNA onto film supports (nitrocellulose or Genescreenplus), the hybridization of each film under the usual conditions with a mixture of probes, and the detection of the radioactive hybrids by contact exposition of the hybridized film onto radiographic film. Another possibility is replicated culture hybridization which involves agarose gel electrophoresis separation of the DNA fragments resulting from treatment of the DNA by restriction enzymes, the transfer of the fragments after alkaline denaturation onto films (nitrocellulose or Genescreenplus) and their hybridization under usual conditions with different mixtures of probes. The formation of radioactive hybrids is detected again by contact exposition of the hybridization support films onto radiographic film.

The radioactive probes are constituted of HPV-DNAs labeled by the "nick translation" method, or by RNAs prepared by transcription of viral DNAs inserted into a vector, for example of the type SP6. The use of radioactive probes offers the advantage of great sensitivity, but this does not exclude the use of non-radioactive probes, for example biotinylated and able to be recognized by antibodies either themselves labeled or themselves recognizable by antibodies bearing enzymatic, fluorescent or other labeling.

The choice of probes depends on the nature of the patient sample. Thus, for example, in the case of a patient suspected of having EV, mixtures 1, 2, 3, 4, 5, 6 and 7 would be used. Mixtures 1 and 2 would permit differential diagnosis between EV and skin warts. Probe 3, which includes the most frequently detected member of each of the three groups of HPVs associated with EV, and probe 7, containing the DNAs of the HPVs associated with cancers of EV, would permit diagnosis of the majority of EV cases and, in particular, the identification of patients infected with the types of HPVs most likely to develop into cancers. The use of mixtures 4, 5 and 6 would distinguish which type or types of HPV are infecting the same patient.

The invention thus again concerns the sets or "kits" containing a number of the probes indicated above, notably:
either the representatives of each of the 19 types and sub-types of HPV-DNAs indicated above;
or mixtures of probes, preferably the diverse groups or mixtures of probes which have been defined above, these kits being intended for diagnostic examinations in vitro by hybridization between the viral preparations obtained from patients, and the diverse groups of mixtures.

As it goes without saying and as it results already anyway from the preceding, the invention is in no way limited to those of its embodiments and applications specifically anticipated, but, on the contrary, embraces all variants, notably the reference in the claims to a designation HPV-DNA followed by a specific number, and to which corresponds an HPV-DNA whose restriction map has been provided in the drawings, is to be understood as signifying that these claims cover all HPV-DNAs which have in common with this particular HPV-DNA, the power to be classed in the same type, according to the definition which was given above, and all the more to HPV-DNAs belonging to the same sub-type.

It is also to be noted, particularly with regard to the DNA derived from HPV-32 which appears in the drawings, that it is not split by any of the following enzymes : AvaI, BalI, BamHI, ClaI, EcoRI, HindIII, NdeI, NruI, PvuII, SacI, SalI, SmaI, TthIII, or XmaI.

Note, too, that the following recombinant DNAs were filed with the C.N.C.M. (National Collection of Cultures of Micro-organisms of the Institut Pasteur in Paris) the 30th of November 1984, under the numbers listed here:

| | |
|---|---|
| pBR322/HPV2d | No. I-379 |
| pBR322/HPV10bA | No. I-380 |
| pER322/HPV10bB | No. I-381 |
| pBR322/HPV14a | No. I-382 |
| pDR322/HPV14b | No. I-383 |
| pBR322/HPV15 | No. I-384 |
| pBR322/HPV17a | No. I-385 |
| pHPV5 HindIIIB/HPV17b | No. I-386 |
| pBR322/HPV19 | No. I-387 |
| pBR322/HPV20 | No. I-388 |
| pBR322/HPV21 | No. I-389 |
| pHPV5 HindIIIB/HPV22 | No. I-390 |
| pER322/HPV23 | No. I-391 |
| pBR322/HPV24a | No. I-392 |
| pBR322/HPV24b | No. I-393 |
| pBR322/HPV28 | No. I-394 |
| pBR322/HPV29 | No. I-395 |
| pBR322/HPV31 | No. I-396 |
| pSP64/HPV32 | No. I-397 |
| pLI55/IP2 | No. I-450 |
| pSP65/1P4 | No. I-449 |

The invention yet more particularly the products of the expression of genes E6 and E7 from the different papillomaviruses which have been evoked in the preceding and which may be used as the active principal of vaccines able to induce, when administered in effective doses, the resistance of the host to the development of neoplasms associated with papillomaviruses.

The invention equally concerns serums susceptible to being obtained by immunization of a mammal, which may be used for the preparation of administrable in effective doses to a patient, notably parenterally, these serums then being able to provoke a remission of the infections induced by the corresponding types or sub-types of papillomaviruses.

It is pointless to emphasize the capacity of the specialist to obtain the products of the polypeptidic expression of the kind in question, notably by the techniques of genetic engineering consisting of the incorporation of the E6 and/or E7 sequences into a vector under the control of an appropriate promoter, then the transformation of a cellular host, of which the papillomaviruses are likely to recognize the promoters in question and to express the sequences associated with it.

The invention thus also concerns the compositions for pharmaceutical usage containing the principles of the kind in question (expression products or corresponding antibodies), in association with a physiologically acceptable pharmaceutical vehicle. In particular, this latter is constituted of an injectable saturated solution, in the case where the compositions of the kind in question will be administered parenterally.

Lastly, reference is made to the articles whose bibliographical references follow, which fill the requirement to describe the prior state of the art to the extent that that proves useful to the complete understanding of this text by the reader. For this reason, the contents of these articles should be considered as being part of the description.

BIBLIOGRAPHY (1) Dürst, M. Et al., 1983, Proc. Natl. Acad. Sci. U.S.A., 80:3812–3815.
(2) Coggin, J. R., Jr. et al., 1979, Cancer Res., 39:545–5 546.
(3) Gissmann, L. et al., 1982, J. Virol. 44:393–400.
(4) Green, M. et al., 1982, Proc. Natl. Acad. Sci. U.S.A. 79:4437–4441.
(5) Heilman, C. A. et al., 1980, Virol. 36:395–407.
(6) Jablonska, S. et al., 1972, Cancer Res., 3:583–589.
(7) Jablonska, S. et al., 1982, Springer Semin. Immunopathol. 5:33–62.
(8) Kremsdorf, D. et al., 1982, J. Virol. 43:436–447.
(9) Kremsdorf, D. et al., 1983, J. Virol. 48:340–351.
(10) Lutzner, M. A. et al., 1978, Bull. Cancer, 65:169–182.
(11) Lutzner, M. A. et al., 1983, Lancet ii:422–424.
(12) Migozzi, M. et al., 1965, Bull. Soc. Franc. Derm. Syph. 72:747–748.
(13) Orth, G. et al., 1980, Cold Spring Harbor Conf. Cell Proliferation, 7:259–282.
(14) Orth, G. et al., 1981, J. Invest. Dermatol. 76:97–102.
(15) Orth, G. et al., 1979, Cancer Res. 39:1074–1082.
(16) Ostrow, R. S. et al, 1982, Proc. Natl. Acad. Sci. U.S.A., 79:1634–1638.
(17) Ostrow, R. S. et al., 1983, Ann. Acad. Dermatol. 1:398–404.
(18) Pfister, H. et al., 1983, Cancer Res. 43:1436–1441.
(19) Pfister, H. et al., 1983, J. Virol. 47:363–366.
(20) Pfister, H. et al., 1981, Int. J. Cancer, 27:645–650.
(21) Rueda, L. A. et al., 1976, Med. Cut. I.L.A. 2:113–136.
(22) Ruiter, M. et al. J. Invest. Dermatol., 47:247–252.
(23) Sutcliffe, J. G., 1978, Nucleic Acids Res. 5:2721–2728.
(24) Tsumori, T. et al., 1983, J. Gen. Virol. 64:967–969.

What is claimed is:

1. A pharmaceutical composition for inducing remission of human papillomavirus (HPV) infection, comprising a. antibodies produced by immunizing a mammal with an immunogenic composition wherein said immunogenic composition comprises a polypeptide encoded by a DNA of a human papillomavirus, wherein said DNA is about 7,000 to about 8,000 base pairs, wherein said human papillomavirus is HPV-31, and wherein said polypeptide is encoded by a human papillomavirus gene selected from the group consisting of E1, E6, E7, L1 and L2; and b. a physiologically acceptable pharmaceutical vehicle.

* * * * *